(12) United States Patent
Nikoonahad et al.

(10) Patent No.: US 6,628,397 B1
(45) Date of Patent: Sep. 30, 2003

(54) APPARATUS AND METHODS FOR PERFORMING SELF-CLEARING OPTICAL MEASUREMENTS

(75) Inventors: Mehrdad Nikoonahad, Menlo Park, CA (US); Shing M. Lee, Fremont, CA (US); Kalman Kele, Santa Cruz, CA (US); Guoheng Zhao, Milpitas, CA (US); Kurt R. Lehman, Menlo Park, CA (US)

(73) Assignee: KLA-Tencor, San Jose, CA (US)

( * ) Notice: Subject to any disclaimer, the term of this patent is extended or adjusted under 35 U.S.C. 154(b) by 0 days.

(21) Appl. No.: 09/396,143

(22) Filed: Sep. 15, 1999

(51) Int. Cl.[7] .............................................. G01N 21/55
(52) U.S. Cl. ...................................................... 356/445
(58) Field of Search ................................. 356/432–447; 250/227.28, 208.2; 134/149; 438/16

(56) References Cited

U.S. PATENT DOCUMENTS

| | | | | |
|---|---|---|---|---|
| 4,218,144 A | * | 8/1980 | Whitehouse et al. .... | 250/208.2 |
| 4,306,835 A | | 12/1981 | Hurley ....................... | 415/118 |
| 4,544,446 A | * | 10/1985 | Cady .......................... | 134/149 |
| 4,672,196 A | | 6/1987 | Canino | |
| 4,710,030 A | | 12/1987 | Tauc et al. | |
| 4,778,995 A | | 10/1988 | Kulpinski et al. ........ | 250/327.2 |
| 5,042,951 A | | 8/1991 | Gold et al. | |
| 5,081,796 A | | 1/1992 | Schultz | |
| 5,159,412 A | | 10/1992 | Willenborg et al. | |
| 5,166,752 A | | 11/1992 | Spanier et al. | |

(List continued on next page.)

FOREIGN PATENT DOCUMENTS

| | | | |
|---|---|---|---|
| EP | 0738561 A1 | 10/1996 | |
| EP | 0824995 A1 | 2/1998 | |
| EP | 0881040 A2 | 12/1998 | |
| EP | 0881484 A2 | 12/1998 | |
| EP | 0886184 A3 | 12/1998 | ............. G03F/7/20 |
| EP | 0886184 A2 | 12/1998 | ............. G03F/7/20 |
| EP | 0890416 A2 | 1/1999 | |
| WO | WO 95/18353 | 7/1995 | |
| WO | WO 98/05066 | 2/1998 | |
| WO | WO 99/02970 | 1/1999 | |
| WO | WO 99/23449 | 5/1999 | |

OTHER PUBLICATIONS

Mehrdad Nikoonahad, Shing Lee, and Haiming Wang, "*Non–Contact System for Measuring Film Thickness*", U.S. patent application Ser. No. 09/028,417, filed Feb. 24, 1998, pp. 43.

Mike Berman, Thomas Bippy, and Alan Smith, "*Review of In Situ & In–Line Detection for CMP Applications*", Semiconductor Fabtech, 8th Edition, www.fabtech.org, pp. 8.

Thomas Bippy and Karey Holland, "*Endpoint Detection for CMP*", Journal of Electronic Materials, vol. 27, No. 10, 1998, pp. 1073–1081.

*Primary Examiner*—Tu T. Nguyen
(74) *Attorney, Agent, or Firm*—Beyer Weaver & Thomas, LLP

(57) ABSTRACT

Disclosed is a self-clearing objective for directing a beam towards a sample and clearing away debris from an optical viewing path adjacent to the sample. The self-clearing objective includes an optical element and a substantially transparent fluid flowing between the optical element and the sample such that at least a portion adjacent to the sample is substantially cleared of debris. The optical element and the fluid cooperatively direct the beam towards the sample. This self-clearing objective may be coupled with various measurement devices to measure various characteristics of samples having debris that prevents clear optical measurements. Additionally, the measurement device may be integrated with or coupled to various sample processing systems so that the relevant process may be clearly monitored.

27 Claims, 6 Drawing Sheets

U.S. PATENT DOCUMENTS

| | | |
|---|---|---|
| 5,181,080 A | 1/1993 | Fanton et al. |
| 5,196,353 A | 3/1993 | Sandhu et al. |
| 5,413,941 A | 5/1995 | Koos et al. |
| 5,433,651 A | 7/1995 | Lustig et al. |
| 5,483,568 A | 1/1996 | Yano et al. |
| 5,596,406 A | 1/1997 | Rosencwaig et al. |
| 5,597,442 A | 1/1997 | Chen et al. |
| 5,643,050 A | 7/1997 | Chen |
| 5,647,952 A | 7/1997 | Chen |
| 5,663,797 A | 9/1997 | Sandhu |
| 5,691,253 A | 11/1997 | Kobayashi |
| 5,747,813 A | 5/1998 | Norton et al. |
| 5,872,633 A | 2/1999 | Holzapfel et al. |
| 5,891,352 A | 4/1999 | Litvak ........................ 216/85 |
| 5,893,796 A | 4/1999 | Birang et al. |
| 5,900,633 A | 5/1999 | Solomon et al. |
| 5,910,842 A | 6/1999 | Piwonka-Corle et al. |
| 5,910,846 A | 6/1999 | Sandhu ........................ 356/381 |
| 5,911,619 A | 6/1999 | Uzoh et al. ..................... 451/5 |
| 5,936,733 A | 8/1999 | Sandhu et al. |
| 5,949,927 A * | 9/1999 | Tang ..................... 250/227.28 |
| 6,122,046 A | 9/2000 | Almogy |
| 6,287,879 B1 * | 9/2001 | Gonzales et al. ............. 438/16 |

\* cited by examiner

APPARATUS AND METHODS FOR PERFORMING SELF-CLEARING OPTICAL MEASUREMENTS

BACKGROUND OF THE INVENTION

The invention relates to apparatus for performing optical measurements on surfaces that are obscured by debris that makes optical measurement difficult.

A wafer surface undergoing chemical mechanical polishing (CMP) is an example of a sample that will typically be obscured by debris that hinders optical measurements of the sample. The wafer is polished by rubbing the wafer between a wafer carrier and pad that is atop a platen. A slurry is typically used to mechanically and chemically facilitate removal of a portion of a film deposed on the wafer's surface. The CMP slurry and residues adjacent to the wafer surface are typically optically inhomogeneous and opaque.

This debris (e.g., slurry and film residue) typically interferes with measurements of the sample. In a polishing process, it is desirable to detect when a film has been partially or completely removed from the wafer. When the film is partially or completely removed, this is usually referred to as the endpoint. It is important to detect the endpoint so that the wafer is not over polished. For example, in copper CMP, the copper film is initially optically opaque. Three endpoints are detected in copper CMP. First, it is determined when polishing of the copper has begun. When the copper film begins to become transparent, this transparency indicates that polishing has started. Second, it is determined when the copper is completely removed so that the underlying liner layer (e.g. Ta, TaN or WN) is exposed. Finally, it is determined when the liner layer has been removed.

When the endpoint of a film is reached, the polishing can then be stopped without polishing away other structures on the wafer. Since there is a lot of debris (e.g., slurry and/or film residue) associated with the CMP process, it would be difficult to accurately measure the endpoint while the wafer is undergoing CMP.

Various approaches to performing in situ optical measurement during CMP have been proposed. However, none of these approaches solve the problem of debris obscuring the wafer. Of note, U.S. Pat. No. 5,433,651 describes a single beam reflectometer employing a window within a cavity of the CMP polishing pad and platen. The described approach has the disadvantage that CMP slurry and residue can build up in the cavity formed within the platen/polishing pad. The slurry and residue make optical measurements difficult. Another approach, described in E.P. Patent 96302176.1, attempts to solve this problem by providing a "soft window" within the cavity where slurry and residue might otherwise accumulate. Unfortunately, this window typically becomes scratched during the polishing process and pad conditioning and thereby also degrades the quality of optical measurements. Also, the material that is used to form the soft window typically scatters the measuring beam.

U.S. Pat. No. 5,081,796 describes moving a small edge portion of the wafer off the edge of the polishing pad, where the removed portion is then exposed to a jet of water which helps guide a beam onto the wafer's edge. However, this approach has the disadvantage of only measuring the film at the edge of the wafer. Since only a small portion of the entire wafer surface is measured, measurement of the endpoint is not very accurate. Furthermore, this procedure may adversely affect the polishing process.

Thus, measurement apparatus and techniques for efficiently and reliably taking optical measurements of samples having associated debris that hinders measurements are needed. More specifically, mechanisms for efficiently removing debris from the measurement path while performing optical measurements are needed.

SUMMARY OF THE INVENTION

Accordingly, the present invention addresses the above problems by providing apparatus and methods for measuring optical characteristics of a sample while clearing debris from the viewing area that is adjacent to the sample. As a result of clearing away debris, the sample may be optically monitored without debris significantly obstructing the optical path. In other words, a measurement beam may be directed towards a sample without being appreciably distorted by debris that may be present adjacent to the sample before and during the measurement process.

In one embodiment, a self-clearing objective for directing a beam towards a sample is disclosed. The objective includes an optical element arranged to direct the beam towards the sample and a substantially transparent fluid flowing between the optical element and the sample such that at least a portion adjacent to the sample is substantially cleared of debris. The fluid also directs the beam towards the sample.

In an alternative embodiment, the optical element and fluid are arranged to cooperatively direct the beam towards the sample. In one embodiment, the fluid is water or a gas. In yet another aspect of the invention, the optical element is in the form of a lens, a system of lenses, a fiber, a fiber bundle, a beam divider, a beam splitter, a beam collimator, a beam polarizer, a wave plate, or any combination thereof.

In another embodiment, the self-clearing objective described above is integrated within a reflectometer device for measuring a reflectivity value of the sample. The reflectometer device includes the self-clearing objective, a beam source arranged to generate the beam and direct the beam through the optical element, through the fluid of the self-clearing objective, and to the sample, and a detector arranged to receive a second beam from the sample in response to the first beam, and analyze the second beam to determine the reflectivity value of the sample.

In another embodiment, the self-clearing objective described above is integrated within an interferometer device. The interferometer device includes the self-clearing objective, a beam source arranged to generate the first beam and a reference beam and direct the first beam through the optical element, through the fluid of the self-clearing objective, and to the sample, and a detector arranged to receive a signal that is a result of interference between the first beam and the reference beam and to analyze the signal to determine a thickness of a film of the sample.

In another embodiment, the self-clearing objective described above is integrated within an ellipsometer device for measuring ellipsometric characteristics of the sample. The ellipsometer device includes the self-clearing objective, a beam source arranged to generate the beam and direct the beam through the optical element, through the fluid of the self-clearing objective, and to the sample, and a detector arranged to receive a second beam from the sample in response to the first beam, and analyze the second beam to determine the ellipsometric characteristics of the sample.

In yet another embodiment, the self-clearing objective described above is integrated within a photoacoustic device for measuring photoacoustic characteristics of the sample.

The photoacoustic device includes the self-clearing objective as describe above, as well as a beam source arranged to generate the beam and direct the beam through the optical element, through the fluid of the self-clearing objective, and to the sample, and a detector arranged to receive a second beam from the sample in response to the first beam, and analyze the second beam to determine the photoacoustic characteristics of the sample. In a preferred embodiment, the detector is further arranged to determine a thickness of films within an opaque film stack deposited on the sample based on the measured photoacoustic characteristics.

In another aspect, the invention pertains to an in-situ chemical-mechanical polishing (CMP) apparatus for polishing a sample with a polishing agent and monitoring the sample. The CMP apparatus includes a polishing table having a viewing opening and a sample mount arranged to hold the sample over the polishing table. The polishing table and sample mount are arranged to receive a polishing agent between the sample and the polishing table and to polish the sample by moving the polishing table and the sample mount relative to each other. The CMP apparatus also includes an optical element proximate the viewing opening. The optical element is configured to receive an optical signal and direct it through the viewing opening to the sample. The CMP apparatus further includes a fluid conduit arranged to receive a fluid between the optical element and the sample to thereby clear away a portion of the polishing agent within the viewing opening such that the optical signal is not substantially altered by the polishing agent before the optical signal reaches the sample.

In a preferred embodiment, the pressurized flow of the fluid is configurable to substantially remove the polishing agent from the viewing opening. In another embodiment, the CMP apparatus also includes a measurement device arranged to detect an endpoint of a film of the sample. For example, the measurement device is either a reflectometer, an ellipsometer, interferometer, or a photoacoustic detector.

The present invention provides several advantages. For example, the self-clearing objective allows a sample to be measured while undergoing a process that may leave debris adjacent to the sample or within the measurement path. This greatly increasing the efficiency of the process since the sample does not have to be removed from the process to be cleaned and then measured outside of the process. Additionally, since the self-clearing objective includes a flowing fluid, it is unlikely to be damaged by an abrasive process, such as CMP. In contrast, a conventional "hard or soft window" is likely to be damaged by an abrasive process, such as CMP (e.g., the window is scratched by the slurry and/or pad conditioning). Additionally, the self-clearing objective does not accumulate scratches that may themselves obscure the sample by scattering the measuring beam, as compared to scratches on a conventional soft or hard window that tend to scatter the measuring beam.

These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to the specific embodiments of the invention. Examples of these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
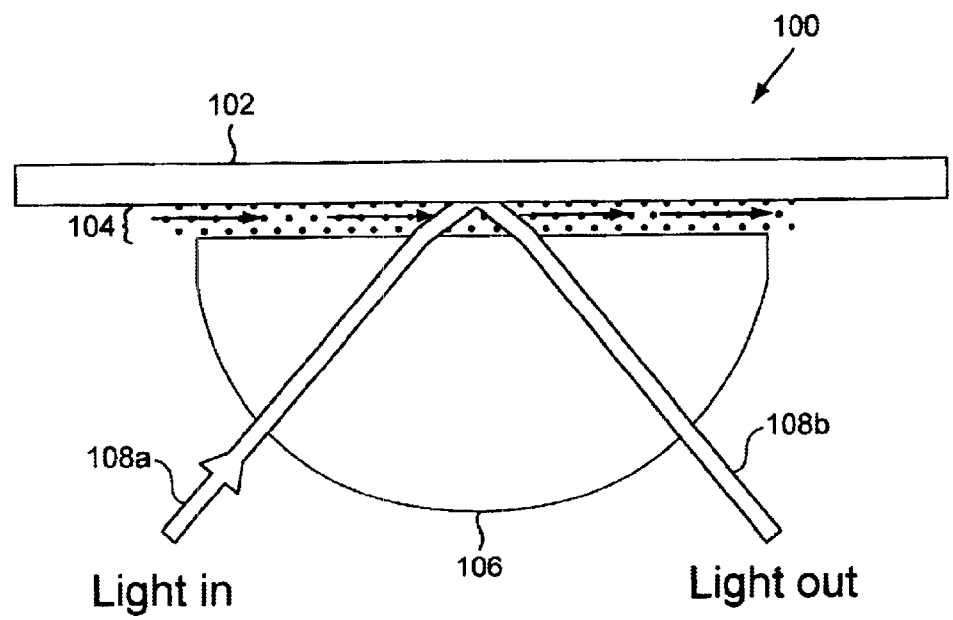
FIG. 1 is a diagrammatic representation of a self-clearing objective in accordance with one embodiment of the present invention.

FIG. 1 is a diagrammatic representation of a self-clearing objective 100 in accordance with one embodiment of the present invention. The self-clearing objective 100 includes an optical element 106 and a flowing fluid 104. The optical element 106 works in conjunction with the flowing fluid 104 to direct an optical beam 108a toward a sample 102. A reflected optical beam 108b may pass through the flowing fluid 104 and optical element 106 to then be detected. The flowing fluid 104 also serves to clear a substantial amount of debris between the optical element 106 and sample 102. The flowing fluid 104 flows between the optical element 106 and the sample 102 such that the optical beam may pass through the optical element 106, the flowing fluid, illuminate the sample 102, and be deflected back along path 108b without significant distortion by debris.

The beam may be any suitable wavelength or plurality of wavelengths of an electromagnetic radiation that can be directed, shaped, focused, collimated, or otherwise modified. As it is to be used to probe the condition of a surface, the beam will be chosen to allow analysis of the surface. Accordingly, the flowing fluid 104 may have any suitable composition that is substantially transparent to the type of radiation used in the beam. For example, the fluid may be composed of water, through which a 400 nm to 1000 nm light beam may pass without significant scattering. However, when the water contains particulates (e.g., from the slurry or polishing residue), a longer wavelength (e.g., 800 to 900 nm) of light may be utilized to reduce scattering by the particulates. Alternatively, the fluid may be selected such that it is merely optically superior to the debris being cleared away (and not necessarily completely transparent to the beam). By way of further examples, the fluid may be liquid or gas, inorganic or organic, etc.

The self-clearing objective may be coupled with any suitable measurement system to clear away debris that obscures measurements of a sample. For example, the self-clearing objective may be coupled with various wafer measurement systems. By way of specific examples, a reflectomer system, an ellipsometer system, an interferometer system, and a photoacoustic system may include a self-clearing objective. Additionally, the self-clearing objective may be used within any sample processing apparatus that causes debris to hinder the measurement being taken of the sample, such as a CMP system which necessarily results in slurry and film residue blocking the measurement path to the sample. For example, photoacoustic characteristics of a sample may be detected and analyzed to determine a thickness of films within an opaque film stack deposited on the sample as it is being polished.

The measurement devices may be configured in various ways. The reflectomer may measure reflectivity using multiple incident beam angles or a single beam angle. Additionally, the reflectometer may measure reflectivity at various wavelengths or a single wavelength. Likewise, the ellipsometer may be configured to measure at any combination of multiple angles, a single angle, multiple wavelengths, and a single wavelength.

Several reflectivity measurement apparatus and reflectivity analysis techniques are described in U.S. Pat. No. 5,747,813 by Norton et al and U.S. patent application Ser. No. 09/298,007 filed Apr. 22, 1999 by Wang et al. Several embodiment of ellipsometer apparatus and methods are described in U.S. Pat. No. 5,910,842 by Piwonka-Corle et al. Photoacoustic systems and methods are described in U.S. application Ser. No. 09/028,417 filed Feb. 24, 1998 by Nikoonahad et al. These patents and patent applications are herein incorporated by reference in their entirety.

When a measurement system with a self-clearing objective is integrated or coupled with a sample processing system, the sample may be clearly monitored as it is being processed. The self-clearing objective of the measurement system provides a mechanism for clearing away debris from a viewing path to the sample. Thus, the sample may be optically monitored without debris obstructing the optical path. Some example processing systems that may utilize a measurement system having a self-clearing objective are epitaxy crystal growth, pipe cleaning, various etching processes, and various wafer processes, such as CMP.

Figure 2:
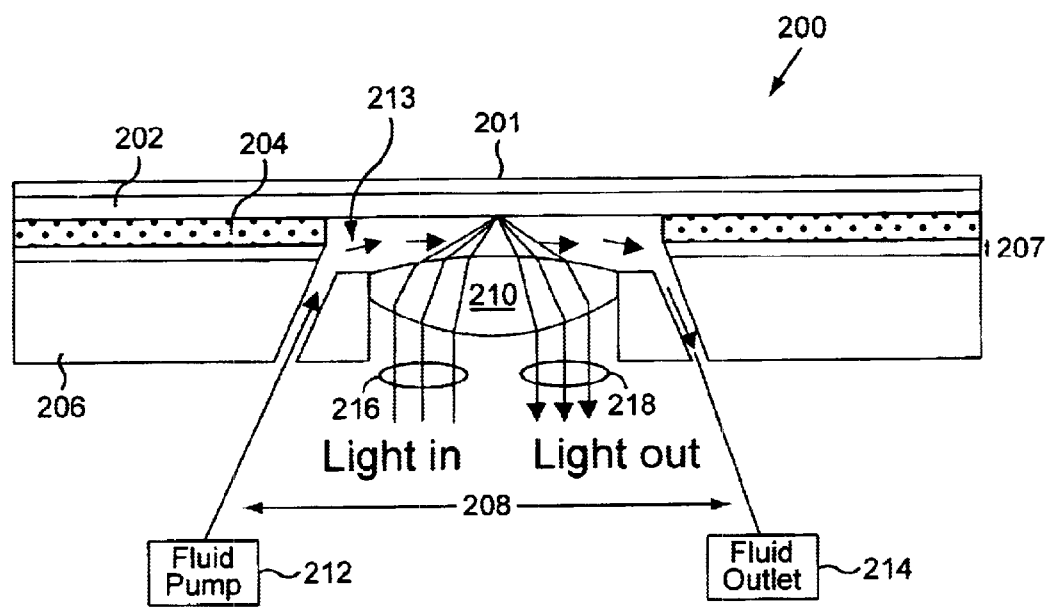
FIG. 2 is a diagrammatic representation of a chemical mechanical polishing (CMP) apparatus that incorporates a measurement system with a self-clearing objective in accordance with one embodiment of the present invention.

FIG. 2 is a diagrammatic representation of a section of a chemical mechanical polishing (CMP) apparatus 200 that incorporates a measurement system (not shown) with a self-clearing objective in accordance with one embodiment of the present invention. The dimensions of the various components are exaggerated to better illustrate the self-clearing objective of this invention. As shown, the CMP apparatus 200 includes a sample holder 201 and a pad 207 and a platen 206 having a hole 208. The sample holder 201 is arranged to hold a sample 202 against the pad 207 and the platen 206. A slurry 204 is placed between the sample 202 and pad 207, which is atop platen 206. When the sample is moved relative to the pad 207, the slurry 204 functions to mechanically and/or chemically polish the sample 202. Of course, any suitable polishing agent may be utilized.

The hole 208 of the pad 207 and platen 206 is configured to contain a self-clearing objective. The self-clearing objective of FIG. 2 includes an optical element 210 and a flowing fluid 213. Any suitable mechanism may be implemented for generating the flowing fluid 213 of the self-clearing objective. As shown, the self-clearing objective also includes a fluid pump 212 and a fluid outlet 214 that generate a constant fluid flow between the optical element 210 and sample surface 202. Alternatively, a fluid pumping system may be implemented within a single device that generates flowing fluid 213. By way of a final example, a ring-shaped hole may be formed around the viewing area into the center of which the fluid is pumped. The fluid then exits through the ring-shaped hole.

The fluid pump 212 may include a control valve (not shown) for adjusting the flow rate. Likewise, the fluid outlet 214 may include a vacuum that provides some control over the fluid flow rate to the fluid outlet 214. The fluid flow rate may be adjusted for different applications or polishing conditions in order to provide different levels of clearing depending upon the specific application. For example, the fluid flow rate may depend on type of slurry, polishing speed, size of fluid reservoir, configuration of optical element, wavelength of light, concentration of slurry, amount of impact on the process, etc. As shown, a slurry 204 that is placed between the pad 207 and the sample 202 is substantially cleared away from the viewing surface of the sample 202 by the flowing fluid 213.

The fluid pump 212 may also include a sensor (not shown) arranged to determine when the sample is near the self-clearing objective. The sensor may utilize pressure, optical, or other inputs to determine sample location. The fluid flow may then be modulated as the sample is near or on top of the self-clearing objective. This arrangement clears the debris along the optical path without overly diluting the slurry adjacent to the self-clearing objective. This prevents the slurry from becoming too diluted to effectively polish the sample.

One or more optical beams 216 may be directed through the optical element 210 and the flowing fluid 213 to the sample 202 to be detected and analyzed. One or more optical beams 218 are then reflected from the sample 202. Optical beams 216 and 218 are not significantly distorted by the slurry 204, as compared to other in-situ measurement systems, since the slurry 204 is cleared away from the optical path by fluid 213 of the self-clearing objective.

Figure 3A:
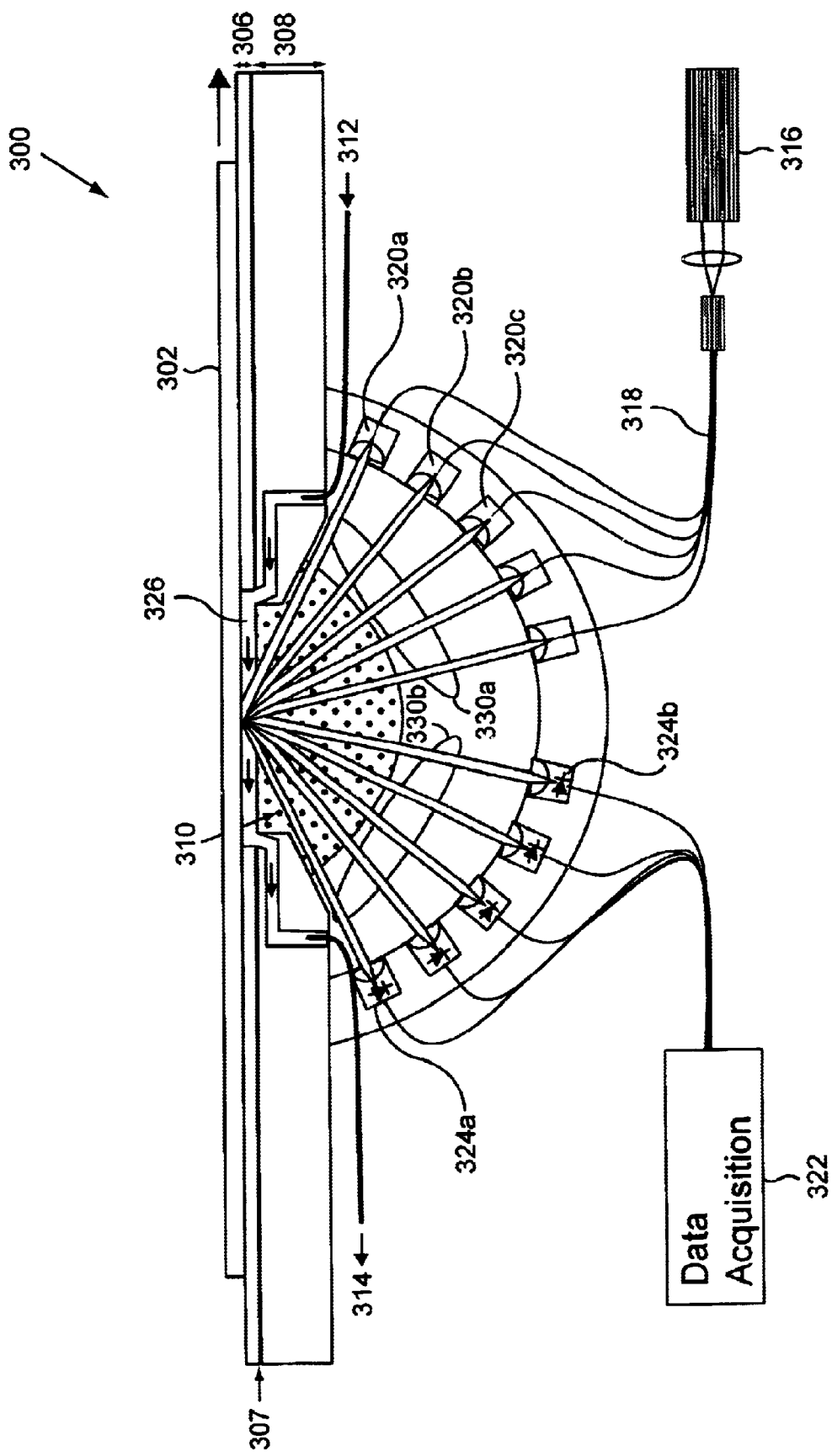
FIG. 3A is side view of a multiple angle reflectometer in accordance with another embodiment of the present invention.
Figure 3B:
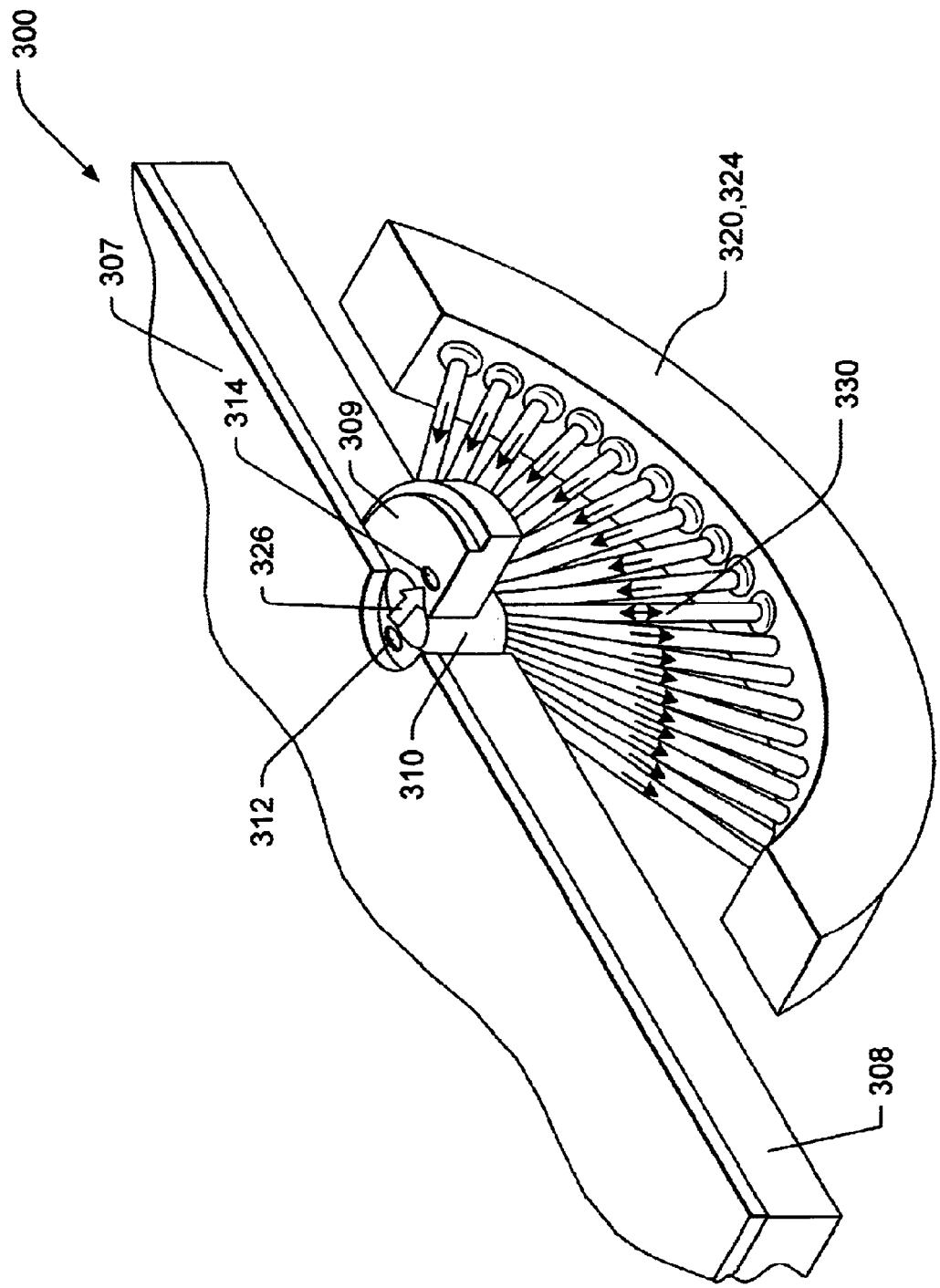
FIG. 3B is a perspective view of the multiple angle reflectometer of FIG. 3A.

FIG. 3A is a side view of a multiple angle reflectometer 300 in accordance with another embodiment of the present invention. A perspective view is also provided in FIG. 3B. As shown, a slurry 306 is placed between a sample 302 and between a pad 307 and an optical element 310. The pad 307 is positioned over a platen 308. As shown in FIG. 3B, the reflectometer 300 also includes a fixture 309 for holding the optical objective 310 in place within the platen 308. As described above, when the sample 302 is moved over the slurry 306 and pad 307, the slurry mechanically and chemically polishes the sample such that a layer is rubbed away from the sample. Of course, any suitable polishing agent may be used.

The polishing results in various debris between the sample surface and the optical element 310. This debris includes slurry which is typically opaque and inhomogeneous. Additionally, a portion of the sample is polished off of the sample during polishing. This residue collects within the slurry. This collection of debris (e.g., slurry and residue) may significantly distort an optical beam that is directed at the sample surface to monitor the polishing process. For example, it may be difficult to use an optical measurement device to detect an endpoint for removal of a particular sample layer from the sample. The fluid serves to clear away some of this debris so that a portion of the sample may be clearly monitored.

The fluid flows into inlet 312, over sample 302, and out of outlet 314. The fluid flow is confined between optical element 310 and the sample 302. Said in another way, the only exit for the fluid flow 326 is through outlet 314. The fluid is effectively pumped through a pipe composed of inlet 312, a narrow channel between the sample 302 and optical element 310, and outlet 314. Fluid pressure may be varied between the optical element 310 and the sample 302 by changing the flow rate into inlet 312 and/or modifying any of the diameters of the inlet 312, channel, and outlet 314, or by changing control system settings.

A plurality of beams 330a are directed towards the sample 302 by beam generator 316. In one embodiment, the beam generator 316 is in the form of a laser source. The laser source 316 may include several laser sources, such as laser diodes, or include a single laser source that is then split into multiple laser beams. The optical beams are collimated by collimators 320. A divergent beam is input into each collimator and output from the associated collimator as a substantially parallel beam.

The optical element 310 may also be configured to tighten the angles between the incoming optical beams (e.g., the optical element is curved with respect to the incident beams). In other words, the angles between the incoming optical beams are greater before the beams enter the optical element, than after the beams exit the optical element. Thus, the angles between the incoming beams may be wider when striking the optical element (e.g., greater than 70 degrees from the normal), as compared with conventional multiple angle systems. Since the total angle spread of the incoming beams is wider, the number of optical beams that are input through the optical element 310 may be enhanced, as compared with conventional systems.

The incoming beams 330a are then reflected off of a sample 302 as a plurality of reflected beams 330b. These reflected beams are then detected by detectors 324, and signals are input into a data acquisition block 322. The data acquisition block 322 may have any suitable configuration of hardware and software for acquiring and analyzing data. The data acquisition block 322 may also include a radio transmitter. In this embodiment, the data acquisition block 322 receives the detected data and then digitizes and transmits the digitized data to a remote receiver and processor for further analysis. A radio transmitter may significantly reduce the number of wires within the reflectometer 300. This arrangement may be useful when one does not wish to run a significant amount of wires out of a system that is rapidly moving (e.g, a rapidly rotating CMP platen).

The intensity or reflectivity values of the reflected beams may then be analyzed to determine various thickness of multiple film layers on sample 302. Any suitable reflectivity analysis may be implemented, and such techniques are well known to those skilled in the art. Several reflectivity measurement and analysis techniques are described in U.S. Pat. No. 5,747,813 by Norton et al., which patent is herein incorporated by reference in its entirety.

Measuring reflectivity at multiple angles provides several advantages over conventional in situ measurement systems that only provide a single angle of incidence. For example, an endpoint may be detected within a CMP system by comparing the relative values of reflectivity. In other words, when the reflectivity values of various incident angles are plotted, the shape of the curve may be analyzed to determine the endpoint. In contrast, conventional systems that utilize a single incident angle must analyze a single absolute reflectivity value, which value may be significantly distorted by slurry and sample residue. Because the amount of signal attenuation caused by such distortion can be impossible to gauge, the measured reflectivity may not provide an accurate account of the surface condition. Thus, the multi-angle embodiment of the invention provides a more reliable detection of the endpoint during a CMP process.

The optical element and/or the flowing fluid may together or separately serve various optical functions, in addition to merely passing the incident beam toward the sample. As described above, the optical element may function to narrow the angles between incident beams. The optical element and/or fluid may shape or direct the incident beam in various ways. For example, the fluid and/or optical element may form one or more lenses, a fiber bundle, beam divider, a beam splitter, a beam collimator, a beam polarizer, a wave plate, or any combination thereof.

Figure 4:
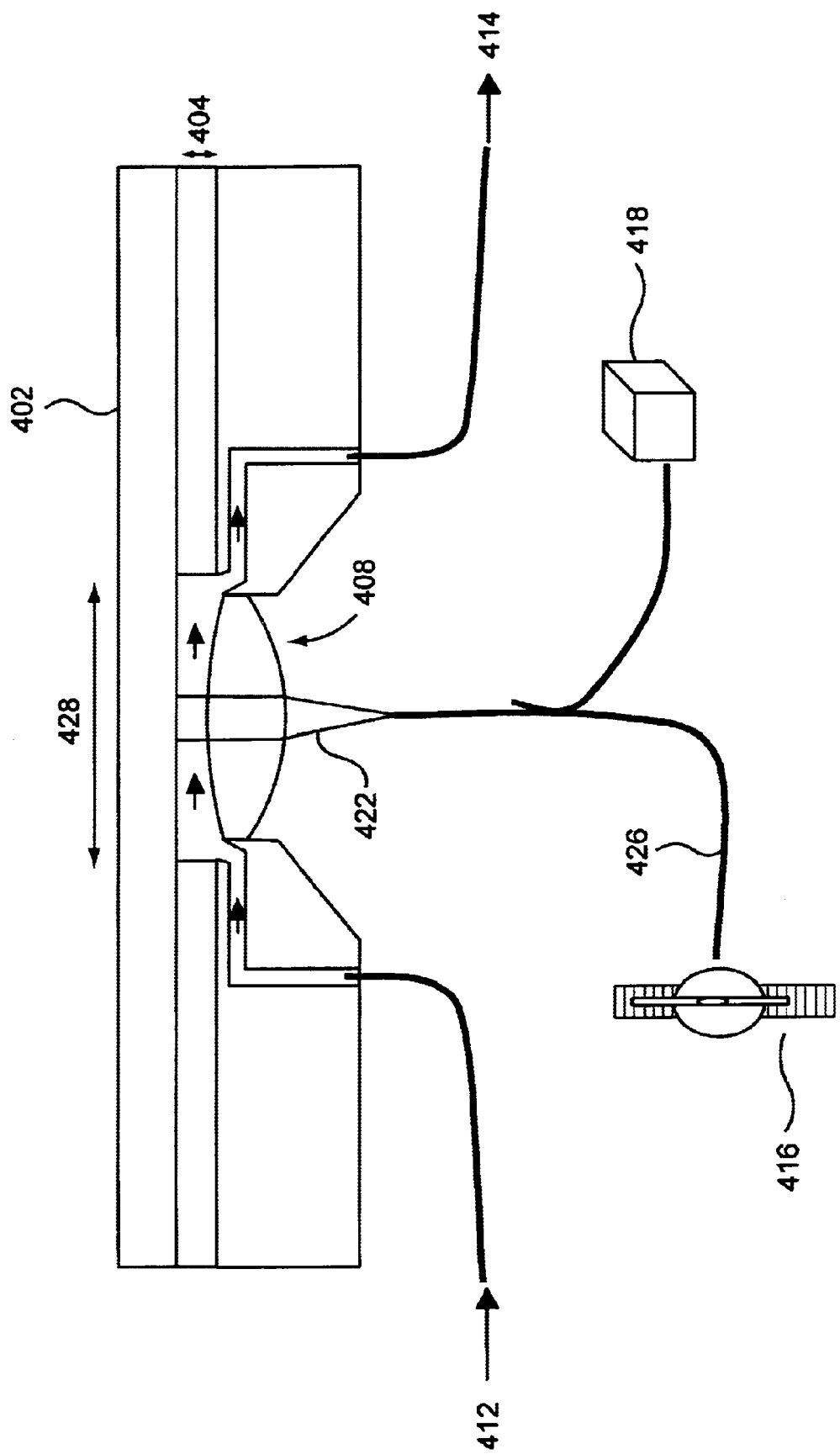
FIG. 4 is a diagrammatic representation of an optical element that functions as a collimator in accordance with one embodiment of the present invention.

FIG. 4 is a diagrammatic representation of an optical element 408 that functions as a collimator in accordance with one embodiment of the present invention. An incident beam is output by source 416 and directed through conduit 426. A divergent beam 422 is input into optical element 408. The optical element 408 collimates the beam 422 and directs it toward the sample 402. A beam that is reflected off the sample 402 is then detected and analyzed by detector and processor 418.

Fluid is also pumped through inlet 412, across surface 428 of the sample 402, and out through outlet 414. Once again, the fluid is pressurized to clear debris 404 from surface 428. Additionally, debris 404 is substantially cleared from the entire optical path of beam 422.

Figure 5A:
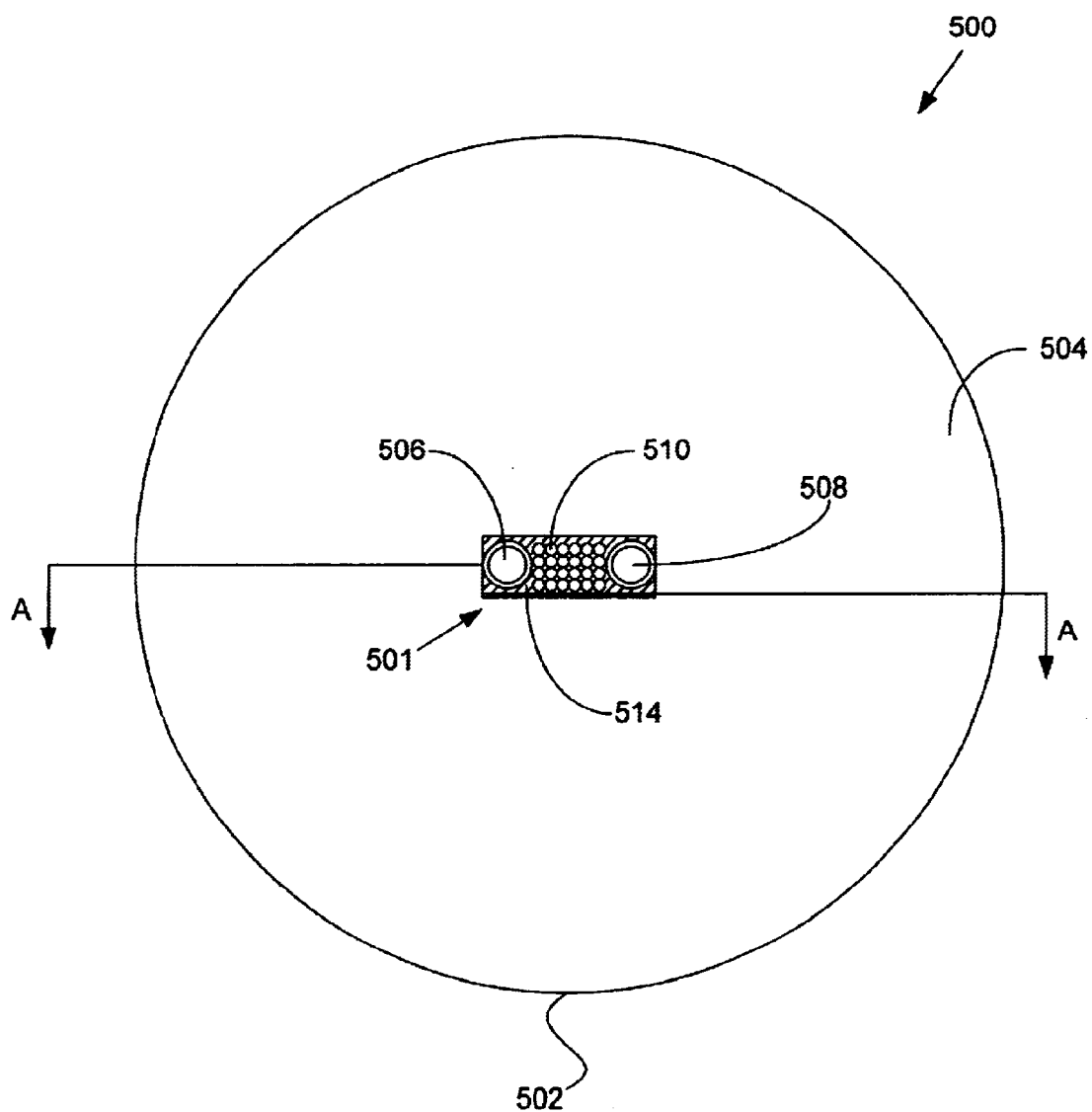
FIG. 5A is a top view of an optical element in the form of a fiber bundle within an in situ CMP measurement device in accordance with one embodiment of the present invention.

FIG. 5A is a top view of an optical element in the form of a fiber bundle 510 within an in situ CMP measurement device 500 in accordance with one embodiment of the present invention. During polishing, a wafer portion may be positioned over hole 501 (which contains elements 506, 508, 510, and 514) of a pad 504 (and platen) so that a measurement may be taken of a film thickness while the wafer portion is substantially cleared of debris. Fluid is pumped onto the underside of the wafer portion through inlet 506 and exits through outlet 508.

A fiber bundle 510 is placed between the fluid inlet 506 and fluid outlet 508 through which measurements are taken of the wafer portion. Preferably, the fiber bundle 510 is flexible so that the movement of the pad 504 and platen does not break the fiber bundle 510. A sealant 514 is placed around the fluid components 506 and 508, as well as the fiber bundle 510. The sealant 514 prevents fluid from escaping from an outlet other then the outlet 508 when a sample is placed over the hole 501. For example, the sealant 514 is placed within hole 501 that contains the fluid components 506 and 508,as well as the fiber bundle.

Figure 5B:
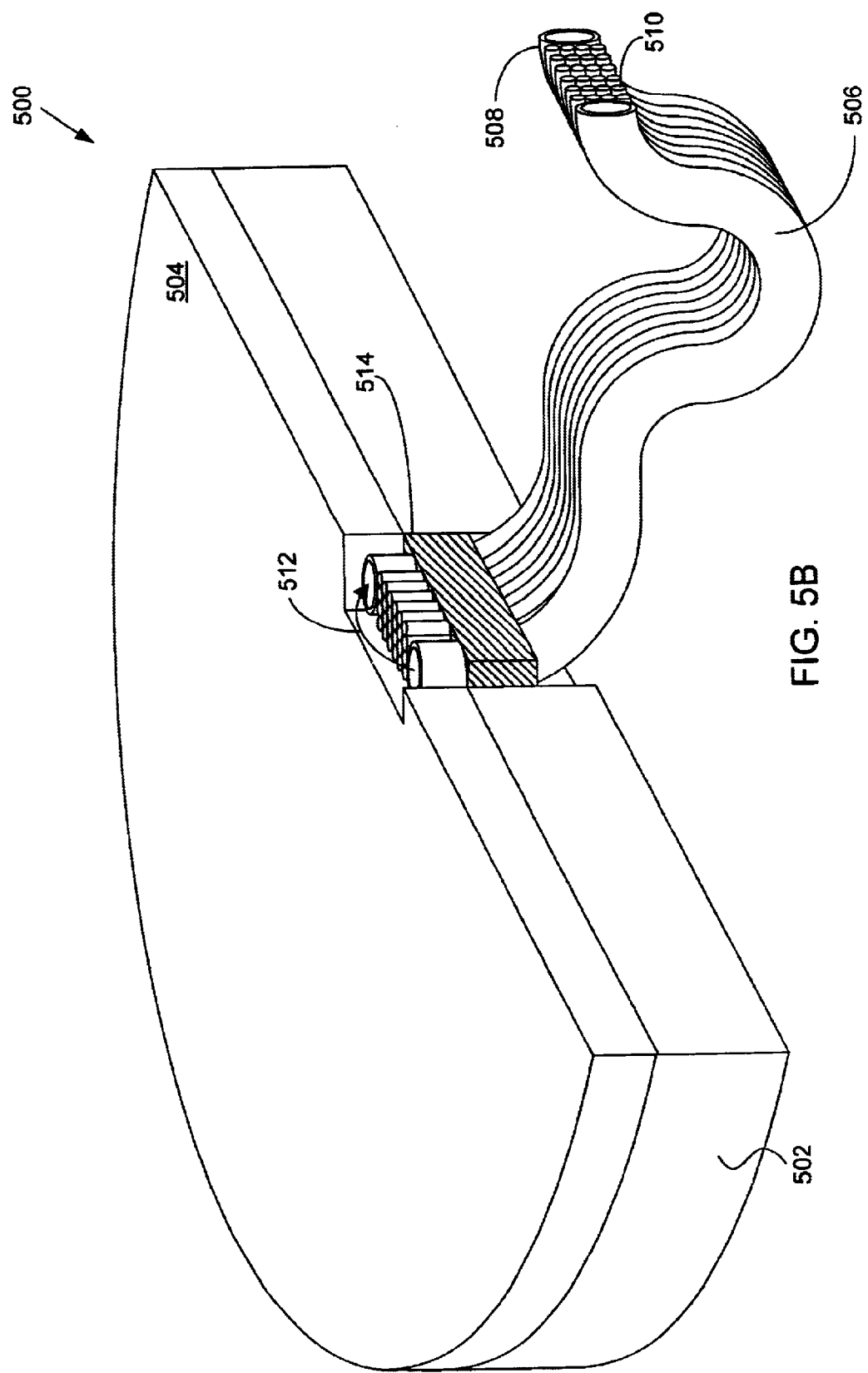
FIG. 5B is cross sectional view of the in-situ CMP measurement system of FIG. 5A in accordance with one embodiment of the present invention.

FIG. 5B is cross sectional view along line A—A of FIG. 5A of the in-situ CMP measurement system 500 in accordance with one embodiment of the present invention. As shown, fluid may be input through tube 506, flow along path 512, and exit through tube 508. The flow path intersects a sample portion (not shown) that is placed atop pad 504. Optical beams are input to the sample through a portion of the fiber bundle 510 and output through another portion of the fiber bundle 510. The sealant 514 is placed around the fiber bundle 510 and the fluid tubes 506 and 508, and between the pad 504 and platen 502.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention.

Accordingly, the present embodiments are to be considered as illustrative and not restrictive, and the invention is not to be limited to the details given herein, but may be modified within the scope and equivalents of the appended claims.

What is claimed is:

1. An apparatus for measuring a characteristic of a sample, comprising:
   an optical element arranged to direct a first beam towards the sample;
   a detector arranged to detect a second beam from the sample, the second beam being at least a portion of the first beam directed away from the sample; and
   a fluid flow mechanism for flowing a substantially transparent fluid in, contact with the optical element and the sample such that only a portion of the sample is substantially flowed over by the fluid and cleared of debris, the portion being where the first beam is directed towards by the fluid and where the second beam is directed away from by the fluid to reach the detector.

2. An apparatus as recited in claim 1 wherein the optical element and fluid are arranged to cooperatively direct the first beam towards the sample.

3. An apparatus as recited in claim 1 wherein an optical path of the first beam is substantially cleared of debris.

4. An apparatus as recited in claim 1 wherein the fluid is water.

5. An apparatus as recited in claim 1 wherein the fluid is a gas.

6. An apparatus as recited in claim 1 wherein the fluid flows in a direction that is substantially transverse to the first beam.

7. An apparatus as recited in claim 1 the fluid flow mechanism comprising:
   a fluid pump for injecting the fluid between the optical element and the sample; and
   a fluid outlet arranged to receive the fluid after it flows proximate the sample.

8. An apparatus as recited in claim 7 further including a sensor arranged to determine when the sample is near the optical element, wherein the fluid pump is also arranged to modulate the fluid flow based on the determination of when the sample is near the optical element.

9. An apparatus as recited in claim 7 further comprising an enclosure positioned around the portion of the sample that is substantially cleared of debris, wherein the enclosure is arranged to receive the fluid from the fluid pump and allow the fluid to exit through the fluid outlet such that the fluid's flow is confined within the enclosure.

10. An apparatus as recited in claim 1 wherein the optical element is in a form selected from one or more of a group consisting of a lens, a system of lenses, a fiber, a fiber bundle, a beam divider, a beam splitter, a beam collimator, a beam polarizer, a wave plate.

11. An apparatus as recited in claim 1, further comprising:
    a beam source arranged to generate the first beam and direct the first beam through the optical element, through the fluid of the objective, and to the sample,
    wherein the detector is further arranged to analyze the second beam to determine the reflectivity value of the sample.

12. An apparatus device as recited in claim 11, wherein the beam source is operable to generate a plurality of first beams at multiple angles of incidence and the detector is operable to analyze a plurality of reflectivity values from a plurality of second beams.

13. An apparatus device as recited in claim 12, the beam source comprising:
    a laser source for providing the plurality of first beams in the form of a plurality of laser beams; and
    a plurality of collimators that each receive one of the first beams, collimate the received first beam, and output the collimated first beam to the optical element.

14. An apparatus device as recited in claim 13 wherein the optical element is further arranged to increase a range of the angles of incidence of the first beams.

15. An apparatus device as recited in claim 11 wherein the beam source and the detector are operable at multiple wavelengths.

16. An apparatus as recited in claims 1, further comprising:
    a beam source arranged to generate the beam and direct the first beam through the optical element, through the fluid of the objective, and to the sample,
    wherein the detector is further arranged to analyze the second beam to determine the ellipsometric characteristics of the sample.

17. An apparatus as recited in claim 16 wherein the beam source and the detector are operable at multiple wavelengths.

18. An apparatus as recited in claim 16 wherein the beam source and the detector are operable at multiple angles of incidence.

19. An apparatus as recited in claim 1, further comprising:
    a beam source arranged to generate the first beam and direct the first beam through the optical element, through the fluid of the objective, and to the sample,
    wherein the detector is further arranged to analyze the second beam to determine the photoacoustic characteristics of the sample.

20. An apparatus as recited in claim 19 wherein the detector is further arranged to determine a thickness of films within an opaque film stack deposited on the sample based on the measured photoacoustic characteristics.

21. An apparatus as recited in claim 1, further comprising:
    a beam source arranged to generate the first beam and a reference beam and to direct the first beam through the optical element, through the fluid of the objective, and to the sample,
    wherein the detector is further arranged to receive a signal that is a result of interference between the first beam and the reference beam and to analyze the signal to determine a thickness of a film of the sample.

22. An apparatus as recited in claim 1 wherein the optical element is arranged to collimate the first beam at a normal angle of incidence relative to the sample.

23. An apparatus as recited in claim 1 wherein the optical element is arranged to facilitate multiple beams at multiple angles of incidence relative to the sample.

24. An apparatus as recited in claim 1 wherein the optical element is arranged to accommodate a plurality of wavelengths for the first beam.

25. An apparatus as recited in claim 1, further comprising:
    a beam source arranged to generate the first beam and direct the first beam through the optical element, through the fluid of the objective, and to the sample,
    wherein the detector is further arranged to transit data based on the second beam to a remote site that is operable to analyze the data to determine the characteristic value of the sample.

26. An apparatus as recited in claim 25 wherein the detector includes a digitizer for digitizing the second beam into data and a radio transmitter for transmitting the data.

27. An apparatus as recited in claim 26 further comprising a receiver arranged to receive and analyze the data.

* * * * *